United States Patent [19]
Janmey et al.

[11] Patent Number: 5,955,434
[45] Date of Patent: Sep. 21, 1999

[54] GEL-FORMING POLYPEPTIDE DERIVATIVES

[75] Inventors: Paul A. Janmey, Arlington, Mass.; Rolands Vegners, Riga, Latvia

[73] Assignee: Brigham & Women's Hospital, Boston, Mass.

[21] Appl. No.: 08/693,215

[22] PCT Filed: Feb. 9, 1995

[86] PCT No.: PCT/US95/01890
§ 371 Date: Jan. 24, 1997
§ 102(e) Date: Jan. 24, 1997

[87] PCT Pub. No.: WO95/21622
PCT Pub. Date: Aug. 17, 1995

[51] Int. Cl.$^6$ ........................... A61K 38/05
[52] U.S. Cl. ........................... 514/19; 530/337
[58] Field of Search ................ 514/19; 530/337

[56] References Cited

U.S. PATENT DOCUMENTS

| | | | |
|---|---|---|---|
| 4,758,550 | 7/1988 | Cardinaux et al. | 514/12 |
| 5,162,512 | 11/1992 | King et al. | 536/6.4 |
| 5,214,195 | 5/1993 | Kung et al. | 560/157 |
| 5,280,113 | 1/1994 | Rademacher | 536/55.2 |
| 5,324,786 | 6/1994 | Kunz et al. | 525/302 |

*Primary Examiner*—Cecilia J. Tsang
*Assistant Examiner*—David Lukton
*Attorney, Agent, or Firm*—Wolf, Greenfield & Sacks, P.C.

[57] ABSTRACT

The invention relates to N-terminal Fmoc-protected peptide combinations that form gels in water and diverse organic solvents, and whose representative overall formulas are: (I), where $R^1$ is $CH_3$, $CH_2$—$CH(CH_3)_3$, $CH(CH_3)CH_2CH_3$, $R^2$ is H, $CH_3$, $CH_2OH$, $(CH_2)_n$—$COOH$, $(CH_2)4$—$NH$—$CO$—$OCH_2C_6H_5$, $R^3$ is dipeptide remainder, m is 0 or 1 and, n is 1 or 2; or (II), where R1 is $CH_3$, $CH_2$—$CH(CH_3)2$, or $CH(CH_3)CH_2CH3$, R2 is $CH2$—$CH(CH3)2$, R3 is H, $CH_3$, $CH_2OH$, $(CH_2)_n$—$COOH$, or $(CH_2)4$—$NH$—$CO$—$OCH_2C_6H_5$, $R_4$ is tripeptide remainder, m is 0 or 1 and, n is 1 or 2. These types of peptides form gels in aqueous solutions and are biologically compatible and may be useful for drug delivery, antigen delivery and may be useful as food additives to retard spoilage and act as fillers.

28 Claims, 9 Drawing Sheets

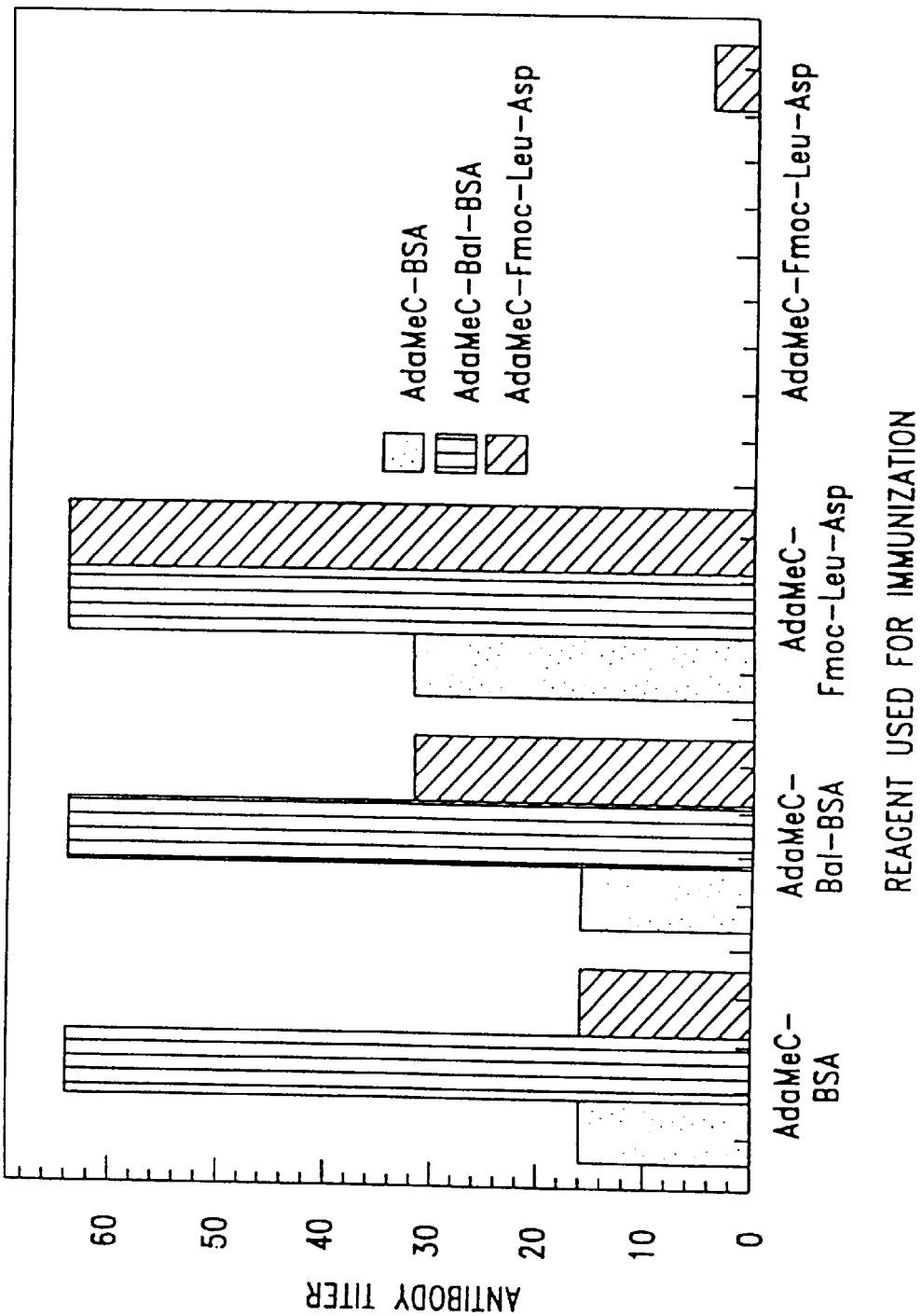

GEL-FORMING POLYPEPTIDE DERIVATIVES

TECHNICAL FIELD

The invention comprises a series of chemically synthesized low molecule weight peptides that form gels in water or organic solvents, as well as the gels so formed. The molecular structure of these gels can be exploited for new materials, stereocatalytic matrices and micelle preparation for research, medical, cosmetic, and food product applications.

BACKGROUND OF THE INVENTION

Gels formed by biocompatible materials have many applications in medicine and industry, but have been limited by the need for high molecular weight compounds, high concentrations of polymer, or organic solvents to form the gels. It would be desirable to synthesize gels that form in aqueous solutions at low concentrations of simple polymers.

A gel consists of continuous networks of molecular aggregates in which solvent molecules are trapped. The gel phase requires stereochemical correspondence between these small molecules in order to generate cohesion. Low molecular weight molecules that form macroscopic gels may do so by a variety of microscopic packings including linear aggregates, micelles, and other structures. Components responsible for the mechanical elasticity of gels may be joined by fragile non-covalent bonds, yielding materials with mechanical properties suitable for pastes or spreads with many cosmetic or therapeutic applications.

High molecular weight network systems are also well described which form gels in water, such as gelatin and starch. These gels form when the macromolecules are mixed with water, heated, and cooled.

There are several examples of low molecular weight compounds that form gels, but predominantly in toxic organic solvents. The chemical structures of such compounds are varied, including for example, organic acids with long aliphatic chains, partially fluorinated n-alkanes, cholesterol derivatives, oxyanthracene derivatives, and others as discussed by Hanabusa, K., et al., *J. Chem. Soc. Chem. Commun.* 4, 390–392 (1993).

Among the low molecular weight compounds that form gels are amino acids and peptide derivatives. Already described in patents to Saito T., et al., Jp. 50022801 (1975) and Saito T., et al., U.S. Pat. No. 3,969,087 (1976) are the structures of amino acid esters and amides containing fatty acids and higher alcohols which form gels in oils and other organic solvents.

Hanabusa K., et al., *J. Chem. Soc., Chem. Commun.* (18)1371–1373 (1992) discloses that the alanine derivative N-benzyl-oxycarbonyl L-alanine 4-hexadecanoyl-2nitrophenyl ester forms thermally reversible gels in methanol and cyclohexane at concentrations below 1%. Similarly, Hanabusa, K., et al., *J. Chem. Soc., Chem. Commun.* 4, 390–392 (1993) discloses that N-benzyloxycarbonyl L-valyl-valine n-octadecylamide makes gels in several organic liquids.

Depsipeptides with the formulas $(X-X^1-OCH_2CH_2COO)_n$ where X and $X^1$ can be valine or isoleucine derivatives form thermostable gels with such solvents as methylene chloride, acetonitrile, ethylacetate, and acetone as discussed in De Vries E. J., et al., *J. Chem. Soc., Chem. Commun.* (3) 238–240 (1993).

Ihara H., et al., *J. Chem. Soc., Chem. Commun.* (17) 1244–1245 (1992) relates to benzyl-oxycarbonyl β-alanine glumamate derivatives in which both carboxyl groups are derivitized with N-dodecylamide groups, dissolve in hot benzene, but on cooling these mixtures form gels. Notably less common are low molecular weight compounds that form gels in water. Among these is the synthetic glycolipid N-octyl-D-gluconamide, which upon prolonged heating in water solutions partly hydrolyses.

It is also noted that t-butoxycarbonyl-valyl-valylisoleucine methylester forms micelles in chloroform in Jayakumar A., et al., *J. Chem Soc., Chem. Commun.* (10) 853–855 (1993). The critical micelle concentration of this peptide is 2.5 mM.

Kalopissis G., et al., French Patent 1,397,231 (1965) discloses asparagine derivatives whose amino groups are acylated by fatty acids and whose amide groups are alkylated. These derivatives form gels in water at concentrations around 3%.

Mandal, A. B. and Jayakumar, J., *J. Chem. Soc., Chem. Commun.* 3, 237–238 (1993) has shown that the tetrapeptide Tyr-Gly-Phe-Ala benzylester diluted in trifluoroacetate/water mixtures forms micelles. While Weitzberg M., et al., PCT Int. Appl. 90 15,602 (1990) and Burch R. M., et al., *Proc Natl. Acad. Sci.,* USA, 88 (2) 355–359 (1991) show that some 9-fluorenylmethoxycarbonyl-(Fmoc-) amino acid derivatives modulate the immune response, Noronha-Blob L., et al., *Eur. J. Pharmacol.,* 199(3) 387–388 (1991) has also shown these derivatives have potential to reduce endotoxic shock.

Notably absent from current gel-forming systems is the ability to rapidly and inexpensively form gels from low molecular weight compounds at low concentrations that are stable in aqueous, non-toxic solutions. Such gels would have many applications in medicine and industry.

SUMMARY OF THE INVENTION

It is the object of the present invention to provide an inexpensive and readily produced biologically compatible gelling substance. This is accomplished by utilizing the newly developed N-terminal Fmoc-protected dipeptide or tripeptide compound series presented here. When placed in an aqueous solution individual dipeptide or tripeptide molecules aggregate in a manner that creates rodlike micelles that can encapsulate other solutes. Similarly shaped micelles have been observed in solutions of larger peptide derivatives, but only in organic solvents as discussed in Mandal A. B., et al, *J. Chem. Soc., Chem. Commun.* (3) 237–238 (1993) and Hanabusa, K., et al., *J. Chem. Soc., Chem. Commun.* 4, 390–392 (1993).

Another object of this invention is to provide a novel delivery system for small hydrophobic or amphiphilic therapeutic molecules. These drugs may range in molecluar weight from approximately 100 Da to approximately 5000 Da. The invention is compatible with either topical or circulatory therapeutics. Many drugs are currently delivered using liposome-based vectors, which are both more expensive to produce and more difficult to create.

A further object of the present invention is to provide a vehicle for injected antigens that boosts their immuno-stimulatory abilities in the absence of conventional crosslinking and adjuvent.

The stable aqueous gels using the dipeptide or tripeptide compounds described herein can also be used, for example, as food additives to retard spoilage by slowing water loss, as food thickening agents, in the purification of proteins by ion exchange chromatography, in the affinity purification of antibodies from serum, and as a malleable cream base for cosmetics.

DETAILED DESCRIPTION OF THE INVENTION

The invention relates to N-terminal Fmoc-protected peptide combinations that form gels in water and diverse organic solvents, and whose dipeptide embodoiment's representative overall formula is:

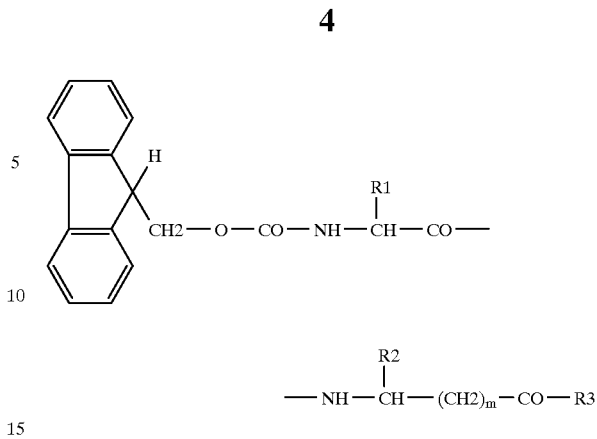

where R1 is $CH_3$, $CH_2$—$CH(CH_3)2$, or $CH(CH_3)CH_2CH3$
R2 is H, $CH_3$, $CH_2OH$, $(CH_2)_n13$ COOH, or $(CH_2)$ 4—NH—CO—$OCH_2C_6H_5$,
R3 is dipeptide remainder,
m is 0 or 1 and,
n is 1 or 2.

Figure 7:
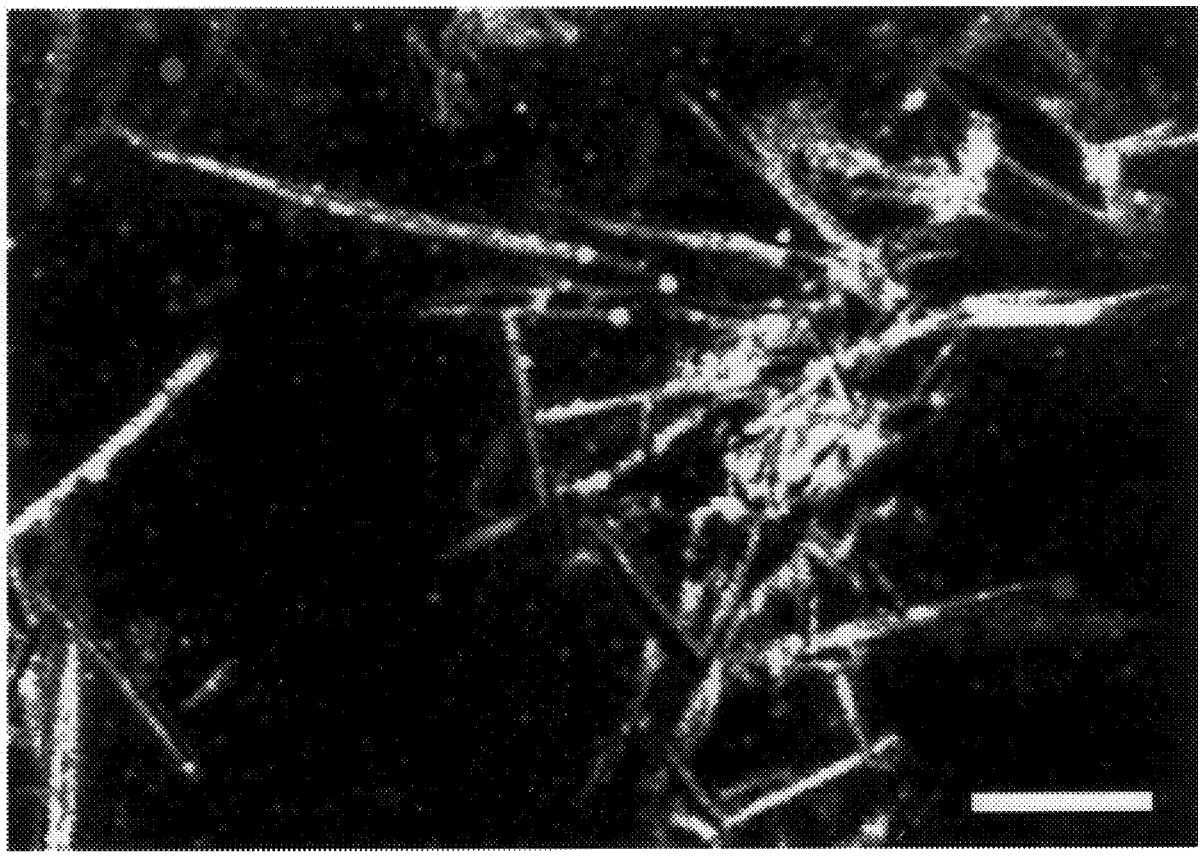
FIG. 7. Confocal scanning micrograph of 4 mg/ml Fmoc-Leu-Asp in 10 mM Tris pH 7.0 containing also 0.02 weight fraction rhodamine-Leu-Asp.

This type of peptide forms gels in water at concentrations less than 1% by weight and is stable between at least 10° C. and 60° C. The gels have elastic moduli on the order of 100 Pa, at peptide concentrations of 2–4 mg/ml, and are characteristic of elastic networks formed by filamentous proteins. The concentration at which Fmoc-Leu-Asp gels form is in the range of the most efficient gelation agents known as shown in Janmey P. A. et al. *Biochemistry* 27, 8218–8227 (1988) and Ferry, J. D. *Ann. NY Acad. Sci.* 408, 1–10, (1983), implying that highly elongated structures must form. Thin rodlike filaments with lengths of 10 microns are visualized by incorporation of trace amounts of rhodamine-Leu-Asp into the Fmoc-Leu-Asp gel as shown in FIG. 7. FIG. 7 is a confocal scanning micrograph of 4 mg/ml Fmoc-Leu-Asp in 10 mM Tris pH 7.0 containing also 0.02 weight fraction rhodamine-Leu-Asp obtained with a BioRad MRC 600 confocal imaging system attached to a Zeiss inverted microscope.

In contrast, gelatin solutions remain sols at such low concentrations, and the lowest concentration of other synthetic polymer gels with comparable shear moduli are at least an order of magnitude higher. Individual examples of this class of peptides form gels in organic solvents such as diethylether, hydrocarbons, and their mixtures.

Figure 6B:
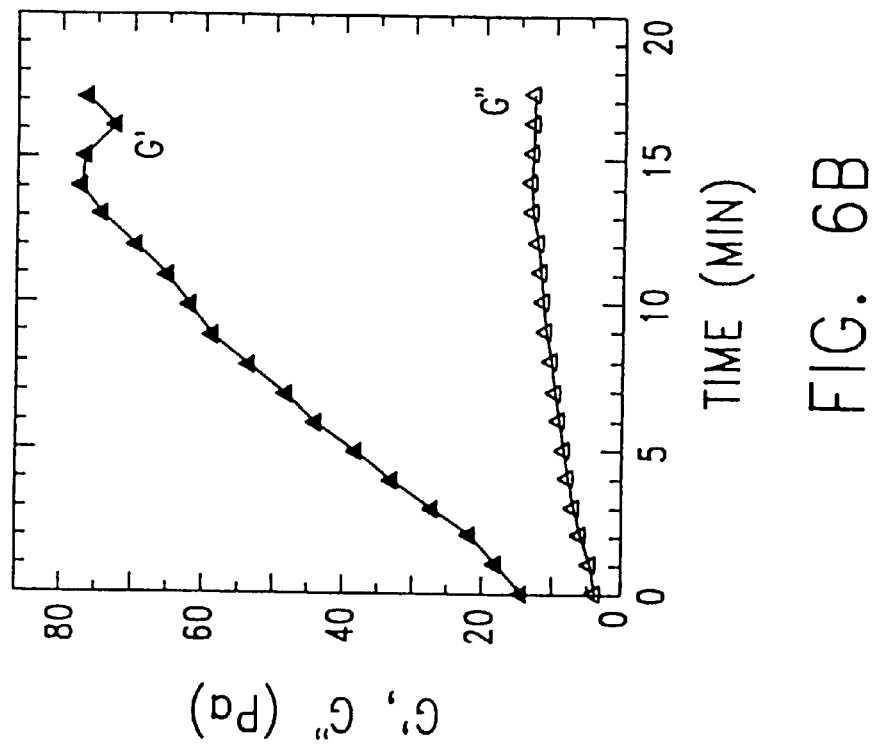
FIG. 6B shows the storage (closed symbols) and loss shear moduli (open symbols) of 2 mg/ml Fmoc-Leu-Asp in 10 mM Tris pH 7.0 at 60° C.
Figure 6A:
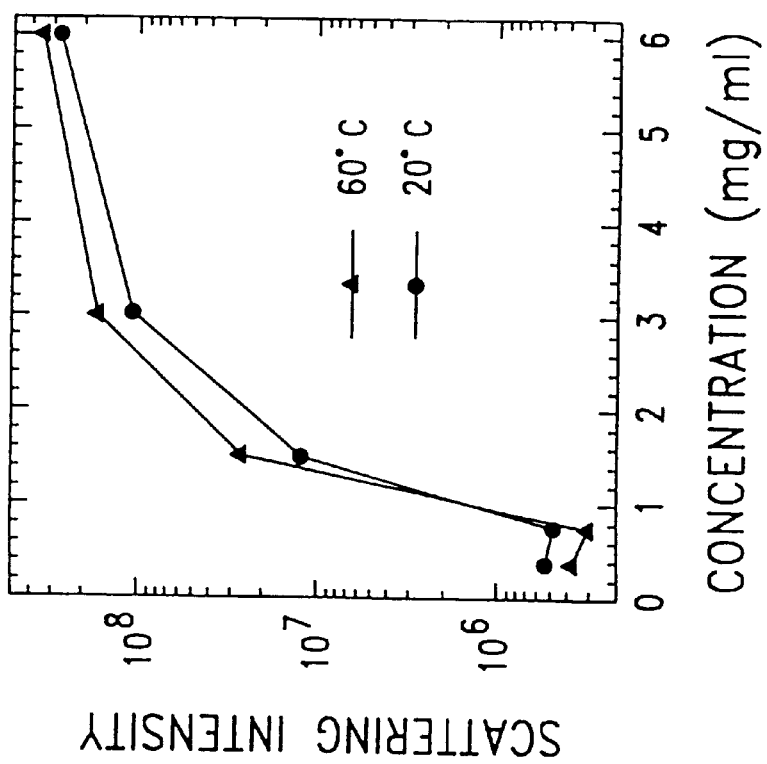
FIG. 6A shows the light scattering intensity of various concentrations of Fmoc-Leu-Asp in 10 mM Tris pH 7.0, measured at 20° C. (circles) and 60° C. (triangles).
Figure 6D:
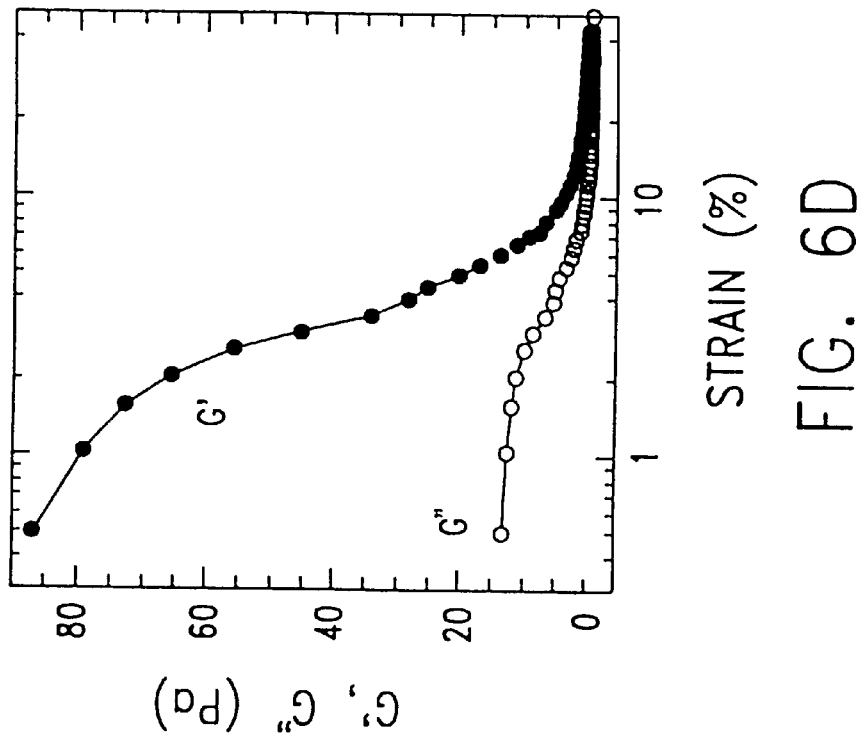
FIG. 6D shows the measurement of G' and G" at various maximal shear strains at a frequency of 1 rad/s. Other experimental conditions and symbols are as described for FIG. 6C.
Figure 6C:
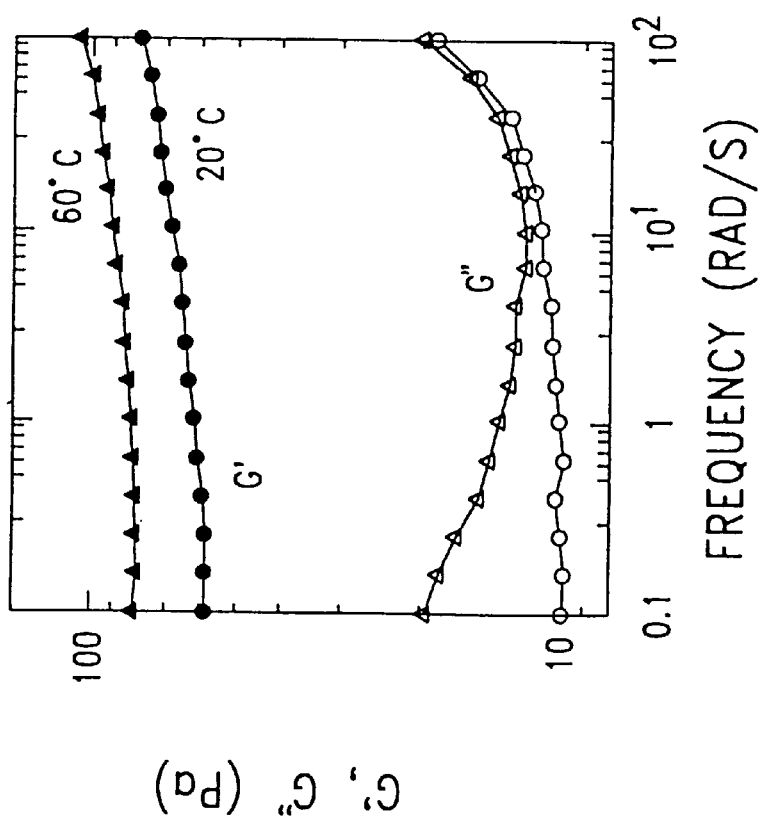
FIG. 6C shows the measurement of shear storage moduls, G' (closed symbols) and shear loss modulus, G" (open symbols) at 1% maximal strain over a range of frequencies at 60° C. (triangles.) and 20° C. (circles). Other experimental conditions are as described for FIG. 6B.

Of particular interest in this invention are the gels formed with Fmoc-Leu-Asp. At concentrations between 1 mg/ml and 1.5 mg/ml solutions of Fmoc-Leu-Asp undergo an abrupt increase in light scattering at both 20° C. and 60° C., as shown in FIG. 6A wherein 1 ml solutions in 1 cm diameter cylindrical cells were measured with a Brookhaven Instruments BI30ATN apparatus using a 633 nm 10 mW laser. When a solution of 2 mg/ml dipeptide is cooled from 100° C. to 60° C., viscoelastic parameters characteristic of a gel are obtained by low strain oscillatory measurements. The storage shear storage modulus, G', a measure of the elastic strength of the material, reaches a stable level of 80 Pa within several minutes (FIG. 6B). These measurements were made using a Rheometrics RFSII instrument1. The maximal shear strain was 1% for oscillatory deformation at a frequency of 1 rad/s. This value is comparable to that of the strongest biopolymer gels, such as fibrin, as shown in Ferry, J. D., *Ann. NY Acad. Sci.* 408, 1–10, (1983) or F-actin, as shown in Janmey P. A. et al., *Biochemistry* 27, 8218–8227 (1988). In contrast, gelatin solutions remain sols at this concentration, and the lowest concentration of other synthetic polymer gels with comparable shear moduli are at least an order of magnitude higher. G', shear storage modulus, depends weakly on frequency from 0.1 to 100 rad/s, and is much larger than the shear loss modulus G" (FIG. 6C). It is also insensitive to temperature, suggesting that structures formed in the dipeptide gel are thermally stable over a physiologically relevant range. However, as FIG. 6D shows, the shear moduli depend strongly on the magnitude of shear deformation. The gels are strain-weakening at the smallest measurable strains (0.3%), and although G' remains>G", both moduli fall by a factor of 100 when the samples are strained to 10%. In this sense, Fmoc-LeuAsp gels differ from fibrin, as shown in Bale, M. D. & Ferry, J. D., *Thromb. Res.*, 52, 565–72 (1988) or F-actin, as shown in Janmey P. A. et al., *Biochemistry* 27, 8218–8227 (1988) gels, as the latter both show strain hardening at 10% followed by rupture and weakening at larger strains. The structural specificity of the gel-forming peptide is summarized in Table 1.

TABLE 1

Fmoc-dipeptides that form aqueous gels

| Sequence | Melting point, °C. | Optical rotation, c = 1; ethanol | Gel formed (minimum conc., %) |
|---|---|---|---|
| Fmoc—Leu—Asp | 158–160 | −8.4 | Yes (0.5) |
| Fmoc—Ala—Asp | 135–137 | −5.2 | Yes (6.7) |
| Fmoc—Ile—Asp | 162–168 | −11.6 | Yes (0.4) |
| Fmoc—Leu—Ala | 168–170 | −26.5 | No |
| Fmoc—Leu—Bal | 150–152 | −25.3 | No |
| Fmoc—Leu—Glu | 100–102 | −16.9 | No |
| Fmoc—Leu—Lys(Cbz) | 98–100 | −12.3 | No |

The partially protected dipeptide Fmoc-Leu-Asp and its analogs set forth in Table 1 were synthesized in 60–80% yield by reaction of the corresponding Fmoc-amino acid-O-succinimidyl esters with sodium salts of amino acids or their derivatives. The reaction was carried out in aqueous DMF, and the peptides were purified by HPLC in an acetonitrile/water gradient.

Further peptide variants of this invention can be synthesized by any of several methods well known in peptide chemistry. One of these methods, used for compound 1 of following table 2 is the following:

An N-protected amino acid N-hydroxysuccinamide ester is formed from an N-protected amino acid and N-hydroxysuccinamide by the carbodimide method in demethylformamide (DMF). The ester is coupled to another amino acid in aqueous KOH solution. After a few hours, the activated ester has reacted and the reaction product can be separated as mentioned in following Example 1.

Other types of activated esters can also be used, other blockers of amino acid carboxyl groups can be used, and other solvents can be employed.

Aqueous gels of the synthesized compounds can be made by several methods which are outlined here and more fully described in the examples.

1. Finely ground dipeptide or tripeptide compound is suspended in boiling water, the mixture is briefly and vigorously mixed or shaken and left to cool. Between 50–60° C. gelation occurs. This procedure can be repeated to obtain a more homogeneous mixture and a stronger gel.

2. The dipeptide or tripeptide compound is dissolved in a minimal volume of organic solvent which is miscible in water, and at room temperature a small volume of the solution is added to a large volume of water with rapid mixing, after which the gel forms.

3. Methods 1 and 2 can be combined.

The amount of Fmoc-protected dipeptide or tripeptide required for gel formation is 0.1% to 5% by weight. The amount of compound incorporated into the gel usually does not exceed 1% and depends on the method of preparation and on other additives in the mixture.

To obtain gels with specific biological effects the gels can be formed in various aqueous suspensions, solutions, and emulsions containing other solutes such as drugs or antigens. Example 4, which follows, describes boric acid-containing gels. Similarly, salicylic acid, S sulfur compounds, and suspensions of therapeutic substances can be incorporated into the gel. Of particular interest, it is noted that compound 5 oof Table 2 forms gels in solutions of 70% glycerol.

The gelatin peptides may also affect the freezing point of the aqueous solutions.

To enhance the activity of various pharmaceuticals and other compounds, these can be incorporated in the gel both physically and chemically. Covalent attachment of immunologically active substances to the gelling peptides may render them more active antigens and the immunostimulatory potential of large polyanions has been exploited to produce antibodies against low molecular weight molecules with little or no intrinsic antigenicity. Antibody production in rabbits against the antiviral drug adamantamine proceeds at least as efficiently when it is trapped in Fmoc-Leu-Asp gels without additional adjuvant as when it is covalently linked to BSA and injected with adjuvant by conventional methods. Additionally, coupling very water soluble compounds can render them less soluble and polyvalent, thereby altering their pharmacokinetics.

The prepared aqueous gels dry more slowly than comparable amounts of gelatin and starch (Example 5 below) and therefore may have novel applications in cosmetic, medical and food product cream compositions.

Figure 1:
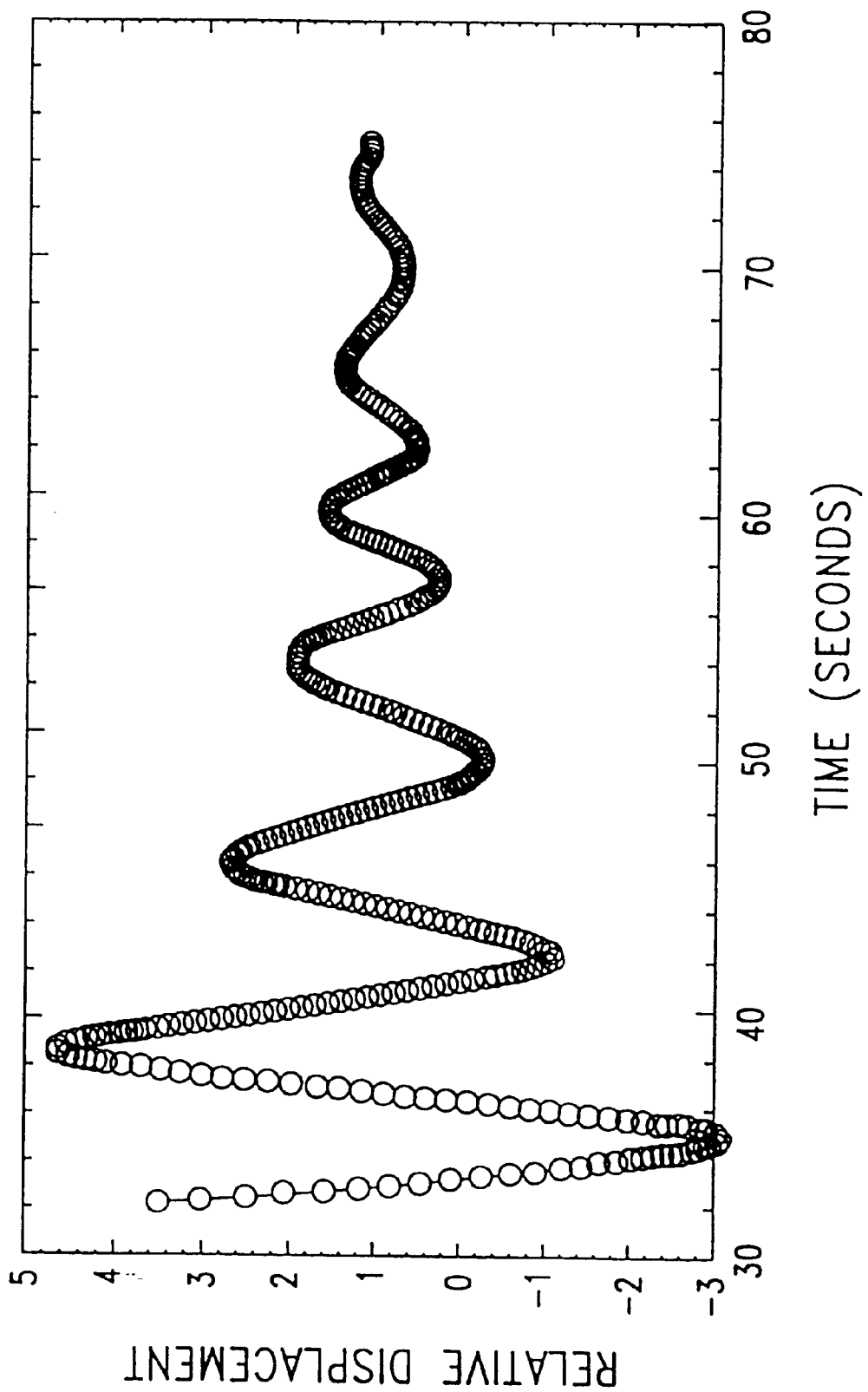
FIG. 1 shows the characteristic oscillatory motion of a solution of the partly protected dipeptide Fmoc-L-Leu-L-Asp (compound 5 of Table 2) obtained from a rheologic measurement using a torsion pendulum. From this curve is calculated the shear modulus $G^1$.

A study of the viscoelastic properties of compound 5 gels are summarized in FIGS. 1, 2, 4 and 6. The shear modulus was measured by free oscillations using a torsion pendulum. The theory and description of the method are described in Plazek D., Vrancke., Berge J., *Trans. Soc. Rheol.* 2, 38–47 (1958); Ferry J. *Viscoelastic Properties of Polymers*, Wiley New York (1980), and Janmey P., et al., *J. Rheol.* 27, 135–153 (1993). Gels are formed by method 1 using Tris buffer pH7.4. The peptide concentration in FIG. 1 is 2.5 mg/ml (0.25%). The shear nodulus derived from these data is 3.1 Pa. This denotes the moderately high elastic strength of this gel.

Figure 2:
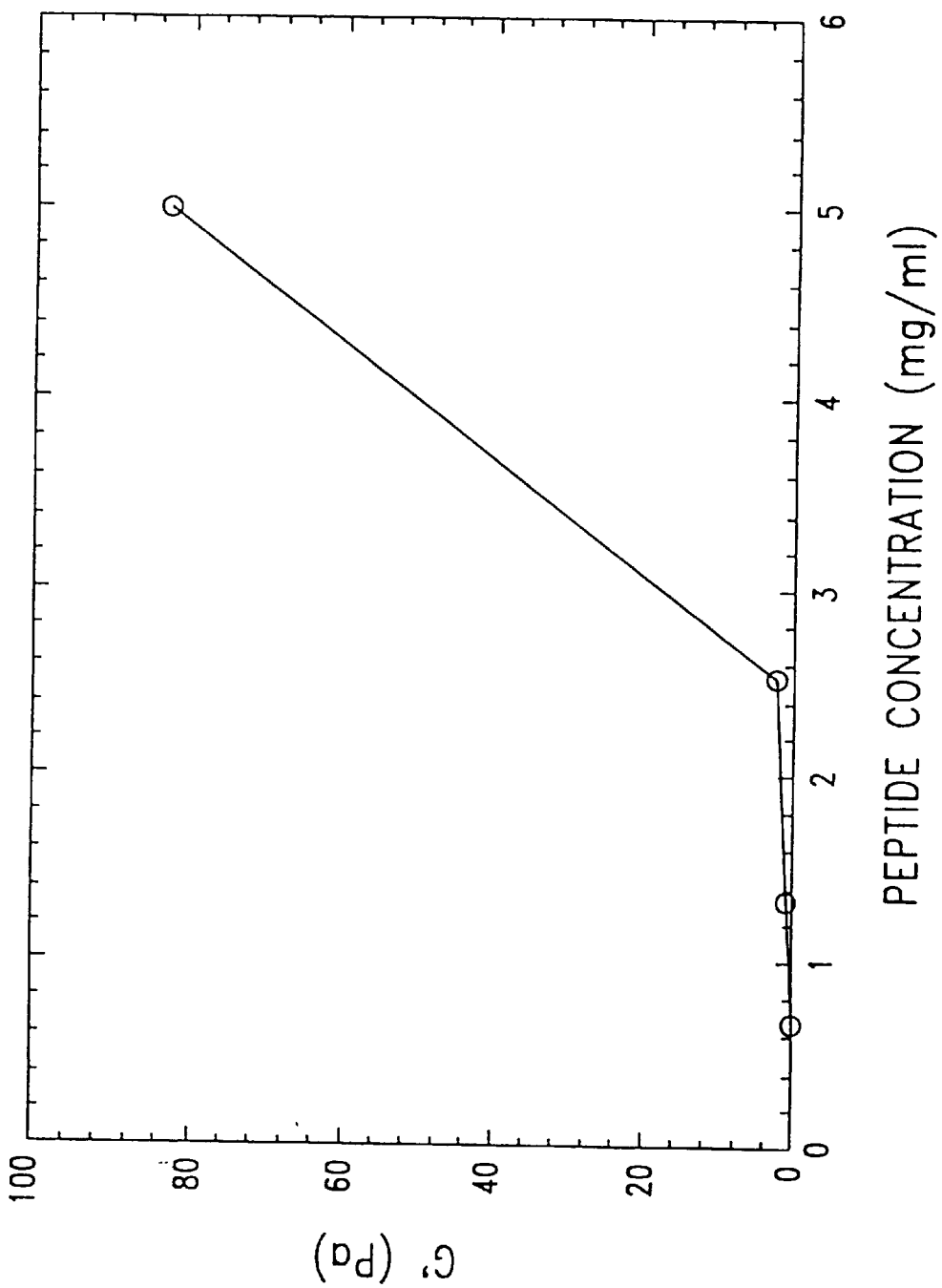
FIG. 2 shows the dependence of $G^1$ on peptide concentration.

The elastic modulus depends on the peptide concentration (FIG. 2). Increasing concentration from 2.5 mg/ml to 5 mg/ml strongly increases the elastic modulus. 5 mg/ml is near the saturation concentration.

Figure 4:
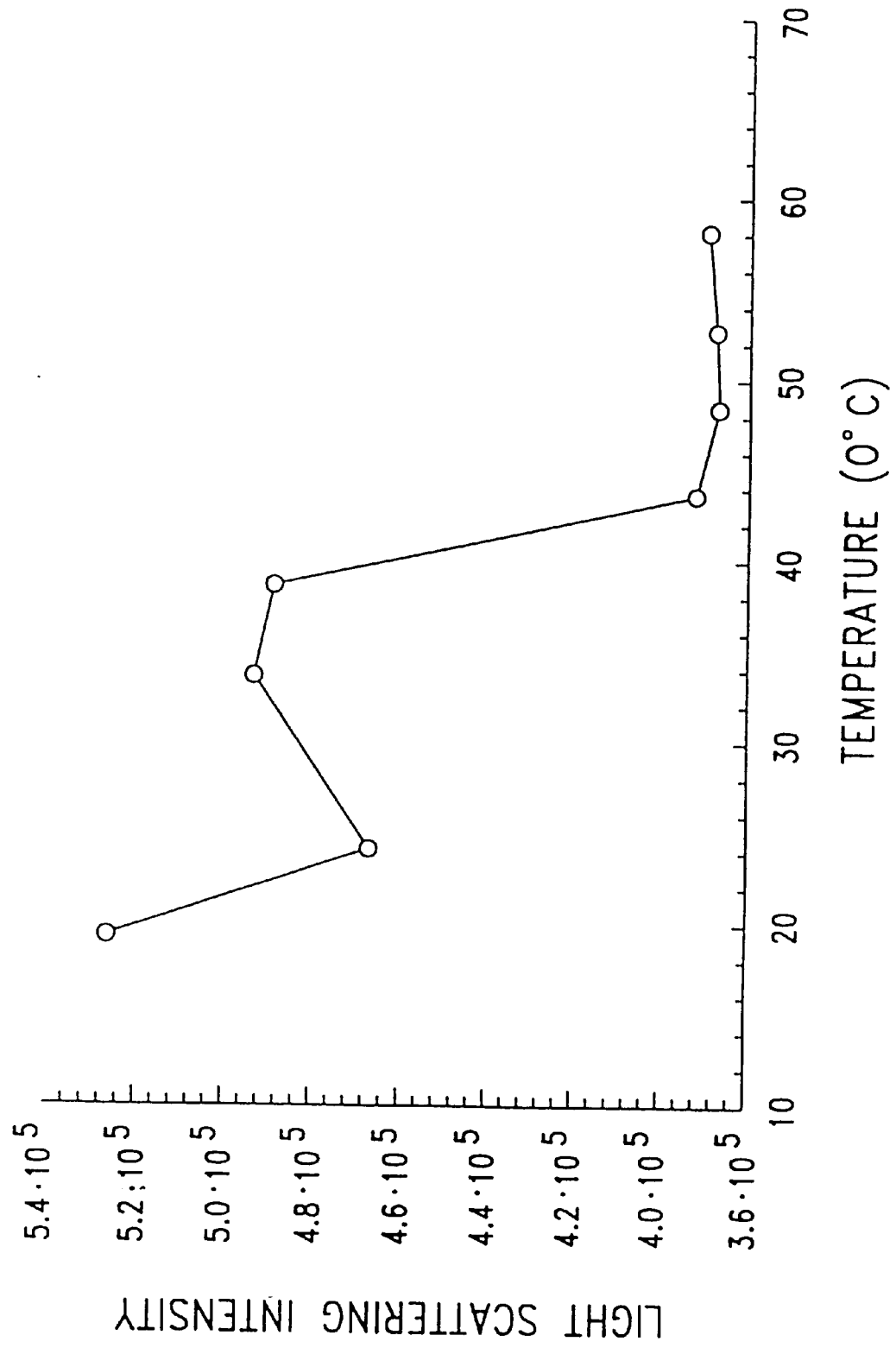
FIG. 4 shows dependence of light scattering intensity on temperature for a compound 5 gel. Experimental parameters: 633 nonometer light, scattering angle—90°, Compound 5 concentration=0.37 mg/ml in 10 mM tris-buffer at pH 7.4.

The dependence of light scattering intensity of compound 5 solutions on peptide concentration and temperature are shown in FIGS. 4 and 6A.

An alternative embodiment of this invention relates to N-terminal Fmoc-protected peptide combinations similar to those discussed above. However, this alternative embodiment is comprised of three peptides and whose overall formula is:

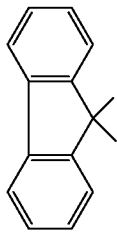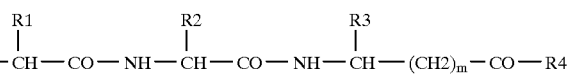

where R1 is $CH_3$, $CH_2$—$CH(CH_3)2$, or $CH(CH_3)CH_2CH_3$
R2 is $CH2$—$CH(CH3)2$
R3 is H, $CH_3$, $CH_2OH$, $(CH_2)_n$—COOH, or $(CH_2)4$—NH—CO—$OCH_2C_6H_5$,
R4 is tripeptide remainder,
m is 0 or 1 and,
n is 1 or 2.

Of particular interest is the Fmoc-Leu-Leu-Asp compound. This compound gels in aqueous solutions of approximately 1% acid. A preferred acid solution for forming gels with this peptide is an aqueous solution of approximately 1% acetic acid. In the absence of acid, the peptide forms aggregates and very weak gels, but the elasticity is strongly increased upon the addition of acid. This feature could be exploited in applications where it would be desirable for a liquid to solidify in an acidic environment. For example, an aqueous mixture of this peptide and a substance to be delivered to the stomach may be taken orally in the liquid form and upon arrival in the acidic environment of the stomach, the mixture would solidify into a gel. It is understood that other than the requirement for an acidic environment, this type of peptide may be used to make gels according to the methods set forth above.

Further details of the invention are shown in the following examples, which are intended to be illustrative, but not limiting of the general characteristics and uses.

EXAMPLES

Example 1

Synthesis of N-protected peptides

Amino acids used, except glycine and b-alanine, are in the L-configuration.

N-protected amino acid (5 mmol) and N-hydroxysuccinimide (5 mmol) are dissolved in a minimal amount of DMF (8 ml) at room temperature or with gentle heating no greater than 45° C. At 0° C. 4 ml of $N_1N^1$-dicyclohexylcarbodiimide (5.5 mmol) in DMF is added. The mixture is kept at room temperature for 1 hour with periodic mixing. Precipitates are removed by filtration and the C-terminal amino acid or peptide (10 mmol) is added from a solution of 2N KOH.

The reaction mixture is vigorously stirred for 2 hours at room temperature. A large volume (100–200 ml) of water is gradually added and the solution acidified with 6N HCl to pH 2.0–3.0. Depending on the particular preparation, a precipitate, gel or oil is formed. A 50–80% yield of the product can be isolated by one of the following methods.

The precipitate is filtered with a glass filter under mild vacuum, rinsed with water, dried under vacuum and, if necessary, reprecipitated from ethylacetate/petroleum ether.

Gels are treated similarly except an appropriate sized (30 cm) glass filter is used.

Oils are taken up in ethylacetate. The ethylacetate phase is washed several times with water, dried with $Na_2SO_2$, and evaporated under vacuum. The remainder is crystallized or reprecipitated.

TABLE 2

Various combinations of peptides synthesized and their properties.

| NO. | Synthetic compound formula 1* | Reactant amino component 2* | Thin-layer Rf (TLC) 3* | Melting Point ° C. | Optical rotation 4* |
|---|---|---|---|---|---|
| 1 | Fmoc—Ala—Asp | Asp | 0.53(3) | 128–130 | −3.9 |
| 2 | Fmoc—ile—Asp | Asp | 0.82(1) | 162–183 | −11.6 |
| 3 | Fmoc—Leu—Ala | Ala | 0.23(2) | 168–170 | −26.5 |
| 4 | Fmoc—Leu-b-Ala | b-Ala | 0.33(2) | 150–152 | −25.3 |
| 5 | Fmoc—Leu—Asp | Asp | 0.80(1) | 158–160 | −8.4 |
| 6 | Fmoc—Leu—Glu | Glu | 0.1(2) | 100–102 | −16.9 |
| 7 | Fmoc—Leu—Gly$_3$ | Gly$_3$ | 0.48(1) | 182–184 | −11.4 |
| 8 | Fmoc—Leu—Lys—(Cbo) | Lys(Cbo) | 0.25(2) | 98–100 | −12.3 |

In Table 2, the following remarks apply:
1* Standard 3 Letter amino acid code. (Cbo) denotes —CO—O—$Ch2C6H5$ group
2* Component 1 is Fmoc—Ala for compound 1; Fmoc—Ile for compound 2; and Fmoc—Leu— for compounds 3–8.
3* Silica gel TLC system:
(1) n-butanol-water-acetic acid 4:1:1
(2) chloroform-ethanol-ethylacetate-acetic acid-water 85:5:8:2:0.25
(3) system(2)-isopropanol 4:1
4* in DMF: dimethylformamide or Ethanol Example 2

Preparation of aqueous gels.

Boil 10 ml water and suspend in it 0.8% finely ground compound 5 of Table 2. Strongly shake or stir the suspension then let stand 10–15 minutes. On cooling the solution becomes turbid at 50–60° C. and at room temperature a gel forms. The gel can be reheated, agitated and recooled. When repeated several times, a stronger gel forms.

Compound 5 is soluble below 0.8%. At concentrations below 0.4% little or no gel forms. When such a solution is evaporated to 50% volume and then heated and cooled, a gel forms.

Example 3

Preparation of gels in ethylether.

Suspend 150–200 mg finely ground compound 5 of table 2 in 10 mL boiling diethylether. Shake suspension, filter and let sit 30–60 minutes at −5° C. On cooling a gel forms. The peptide concentration can be measured by weighing the gel, and evaporating the solvent in vacuum to a constant weight. In this way a solute concentration of 1–1.2% was found.

Example 4

Gel of compound 5 and boric acid.

Add 0.8% compound 5 to 3.5% boric acid in boiling water and shake. On cooling, a gel forms. The gel can be smeared on a glass plate to a thickness of 1–2 mm. When the water evaporates, a uniform film containing the boric acid is formed.

Example 5

Gel drying.

Figure 5:
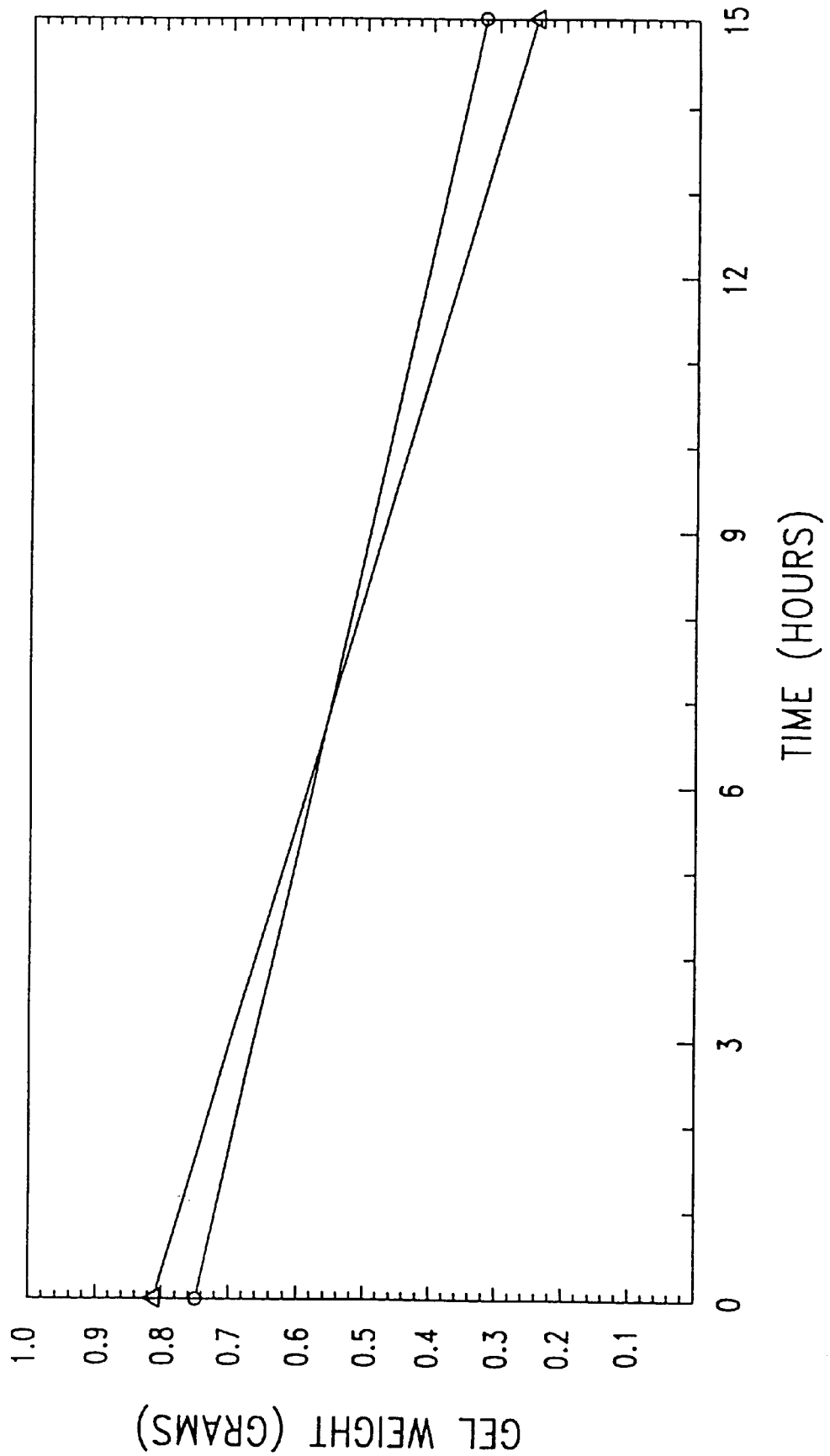
FIG. 5 shows the effects of compound 5 and gelatin on the evaporation of water.

Gels containing either 0.5–0.6% or 0.8% compound 5, gelatin, or starch are disolved in water at 90° C. and briefly cooled. The solutions (0.8 ml) are poured into shallow plastic dishes (17 mm inner diameter). On reaching room temperature, the dishes are weighed and left with desicants but without vacuum to dry. Only compound 5 forms a gel on cooling. After 15 hours, the compound 5 gel has lost 57% of its water, but the gelatine and starch solutions have lost 70% and 87% of their water, respectively. The effects of compound 5 and gelatin are shown in FIG. 5. Gelatin is less effective than compound 5 at retarding the evaporation of water.

Example 6

Incorporation of antigenic agents into gels and stimulation of immune response.

In discussion of this example, the following abbreviations are used:

Ada2Me: 3,5-dimethyl-1-adamantanamine hydrochloride,

AdaMeC: 5-methyl-1-adamantanamine 3-carboxylic acid hydrochloride,

AdaMeC-BSA: conjugate of bovine serum albumin and AdaMeC prepared by the carbodiimide method, AdaMeC-Bal-BSA: conjugate of bovine serum albumin and AdaMeC-(beta-alanine) with a free amino group.

The low molecular weight drugs 3,5-dimethyl-1-adamantanamine hydrochloride (Ada2Me) and 5-methyl-1-adamantanamine 3-carboxylic acid (AdaMeC) can also be incorporated into the Fmoc-Leu-Asp gels (10 mg/ml=21 mM) at concentrations of 1 mM and 33 mM, respectively. At higher total concentrations, (>5 mM Ada2Me or >33 mM AdaMeC) these agents inhibit gelation. When the Fmoc-Leu-Asp gel containing AdaMeC in phosphate buffered saline was injected into rabbits, without adjuvant, antibodies were raised against this drug to produce antisera with titers as high or higher than those of animals immunized with AdaMeC-BSA conjugates in equal volumes of complete Freund's adjuvant (FIG. 8). Three methods of antibody determination, double diffusion in agarose gel, reverse radial diffusion, and passive hemagglutination gave comparable results. Injected alone, neither Ada2Me (5 mM) nor AdaMeC (33 mM) produced specific antibodies. Fmoc-Leu-Asp alone produced antibodies with titers no greater than 1:4.

Figure 8B:
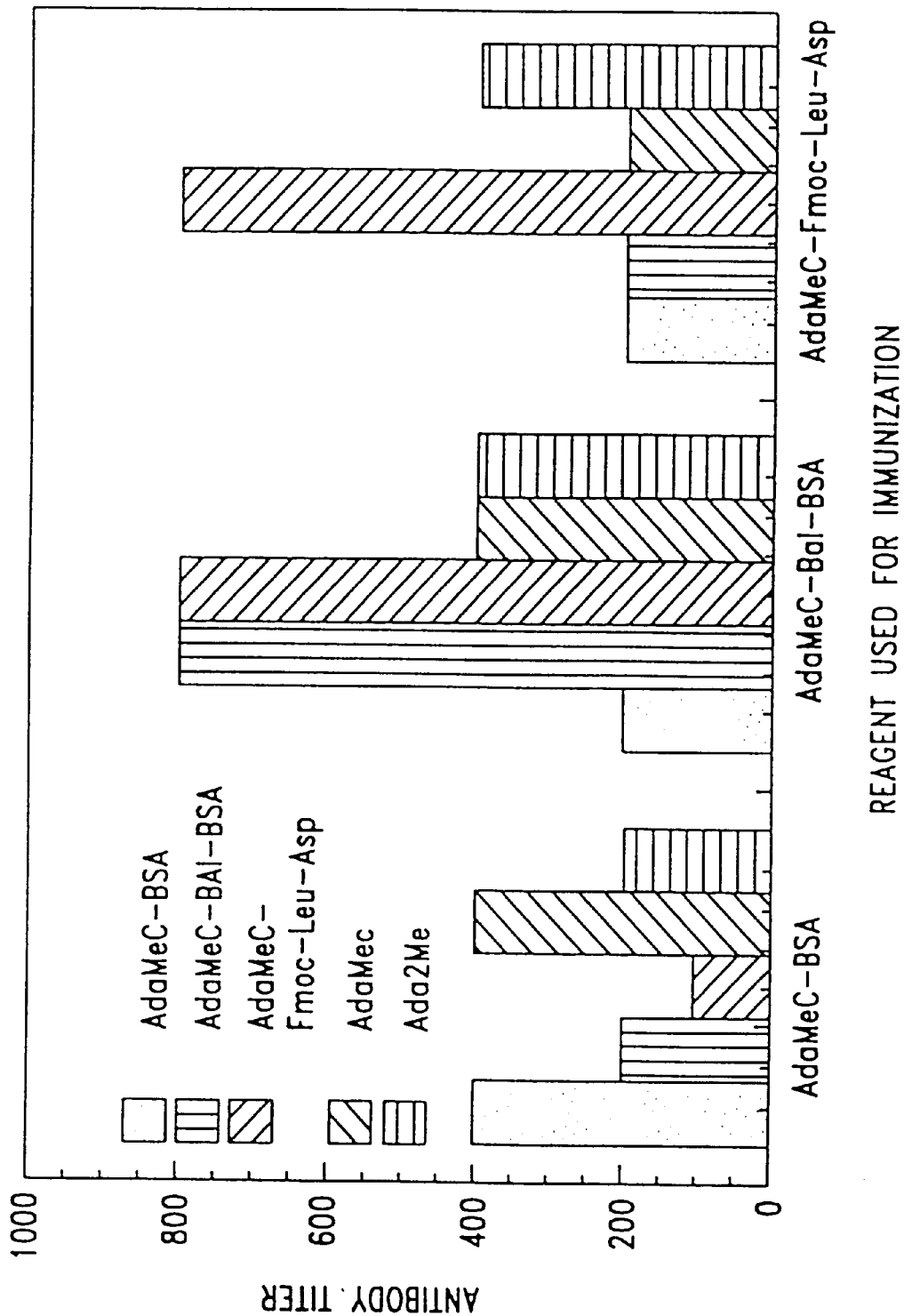
FIGS. 8A and B show the development of antibodies against 5-methyl-1adamantanamine 3-carboxylic acid hydrochloride (AdaMeC) using Fmoc-Leu-Asp.

Female random-bred rabbits were immunized three times, at weekly intervals and bled on the 24th day. A full dose was used for the first two immunizations, and a half of the full dose for the third immunization. Full doses of the BSA conjugates were 100 μg total protein. Before injections, AdaMeC-BSA and AdaMeC-Bal-BSA solutions were diluted with equal volumes of complete Freund's adjuvant, but AdaMeC+dipeptide gel was diluted with an equal volume of 0.01M phosphate buffer; pH 7.4. The volume of immunogen solutions injected each time was 1 ml. Immune sera were analyzed by two immunoprecipitation assays, the double diffusion in agarose gel and the reverse radial immunodiffusion, as described by Oudin, J. *Meth. Enzymol.*, 70, 166–98 (1980). As shown in FIG. 8A double diffusion in agarose was used to determine the titer of antibodies recognizing AdaMeC-containing conjugates in sera of rabbits immunized with AdaMeC-coupled with or without a beta-alanine (Bal) spacer to BSA in complete Freunds adjuvant or with AdaMeC mixed with Fmoc-Leu-Asp without adjuvant. The antisera were tested against each of the three immunogens and compared to sera of rabbits injected with either AdaMeC or Fmoc-Leu-Asp-alone. And as shown in FIG. 8B the passive hemagglutination test, as described in Adler, F. L. & Adler, L. T., *Meth. Enzymol.*, 70, 455–66 (1980), was used to analyze antisera of rabbits immunized with each of the three AdaMeC conjugates after challenge with the three AdaMeC conjugates, AdaMeC alone or Ada2Me. In the first two assays, the solid phase was 1% agarose containing 0.8% sodium chloride. The sample volumes were 25 μl. The probes were incubated for 72 h at 37° C. In double diffusion in agarose gel, the antigens were placed in central wells and the antisera in surrounding wells in concentrations between 20 μg/ml and 1000 μg/ml which included also the equivalent balanced concentration. In the reverse radial immunodiffusion assay, Ada2Me or AdaMeC was mixed with agarose in concentrations between 20 μg/ml and 200 μg/ml, and the antisera were placed in wells in various concentrations. In control experiments, sera of non-immunized animals were used. In the passive hemagglutination reaction, 0.5% suspensions of sheep red blood cells were treated with seven preparations: two BSA conjugates [AdaMeC-BSA, AdaMeC-BalBSA], BSA alone, Ada2Me+dipeptide gel, the dipeptide gel alone, and Ada2Me or AdaMeC alone. The protein concentration in the BSA preparations was 1 mg/ml. In the case of the dipeptide gel preparations, 0.5 ml of the gel was mixed with 4.5 ml of a suspension of SRBC. Ada2Me was applied in a concentration of 200 μg/ml. The mixtures were incubated for 1 h at 20° C., the unadsorbed antigens were removed by centrifugation, SRBC were washed. Samples of 50 μl were placed in the wells of the trays. Antisera and purified antibodies were diluted with 0.01M phosphate-buffered saline, pH 7.4 starting from 1:100 with a step of ½. Untreated SRBC, sera and antibodies from non-immunized animals were used in control experiments.

We claim:

1. An F-moc derivatized anionic dipeptide of the general formula:

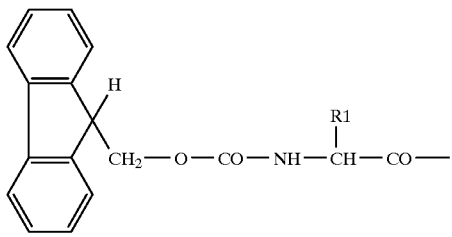

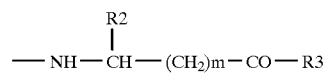

wherein:

R1 is selected from the group consisting of CH₂—CH (CH₃)₂ and CH(CH₃)CH₂CH₃;

R2 is selected from the group consisting of H, CH₃, CH₂OH, (CH₂)ₙ—COOH, and (CH2)₄—NH—CO—OCH₂C₆H₅;

R3 is OH;

m is either 0 or 1; and n is either 1 or 2.

2. The dipeptide of claim 1 wherein R2 is CH₂—COOH.

3. The dipeptide of claim 2 wherein R1 is CH₂—CH (CH₃)₂.

4. The dipeptide of claim 2 wherein R2 is CH(CH₃) CH₂CH₃.

5. An aqueous gel comprising water and 0.1% to 5.0% by weight of the dipeptide of claim 1.

6. An aqueous gel comprising water and 0.1% to 1.0% by weight of the dipeptide of claim 1.

7. An aqueous gel comprising water and 0.1% to 1.0% by weight of the dipeptide of claim 2.

8. An aqueous gel comprising water and 0.1% to 1.0% by weight of the dipeptide of claim 3.

9. An aqueous gel comprising water and 0.1% to 1.0% by weight of the dipeptide of claim 4.

10. The aqueous gel of claim 5 further comprising an antigen.

11. The aqueous gel of claim 5 further comprising a low molecular weight drug.

12. The aqueous gel of claim 11 wherein the low molecular weight drug is selected from the group consisting of 3,5-dimethyl-1-adamantanamine hydrochloride and 5-methyl-1-adamantanamine 3-carboxylic acid.

13. An F-moc derivatized anionic dipeptide of the general formula:

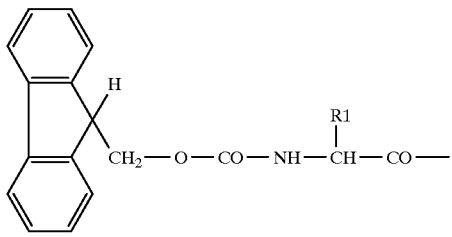

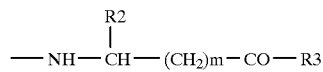

wherein:

R1 is selected from the group consisting of CH₃, CH₂—CH(CH₃)₂ and CH(CH₃)CH₂CH₃;

R2 is selected from the group consisting of CH₂OH, (CH₂)ₙ—COOH, and (CH2)₄—NH—CO—OCH₂C₆H₅;

R3 is OH;

m is either 0 or 1; and n is either 1 or 2.

14. The dipeptide of claim 13 wherein R2 is CH₂—COOH.

15. The dipeptide of claim 14 wherein R1 is CH₂—CH (CH₃)₂.

16. The dipeptide of claim 14 wherein R1 is CH₃.

17. The dipeptide of claim 14 wherein R2 is CH(CH₃) CH₂CH₃.

18. An aqueous gel comprising water and 0.1% to 5.0% by weight of the dipeptide of claim 13.

19. An aqueous gel comprising water and 0.1% to 1.0% by weight of the dipeptide of claim 13.

20. An aqueous gel comprising water and 0.1% to 1.0% by weight of the dipeptide of claim 14.

21. An aqueous gel comprising water and 0.1% to 1.0% by weight of the dipeptide of claim 15.

22. An aqueous gel comprising water and 0.1% to 1.0% by weight of the dipeptide of claim 15.

23. An aqueous gel comprising water and 0.1% to 1.0% by weight of the dipeptide of claim 17.

24. The aqueous gel of claim 18 further comprising an antigen.

25. The aqueous gel of claim 18 further comprising a low molecular weight drug.

26. The aqueous gel of claim 25 wherein the low molecular weight drug is selected from the group consisting of 3,5-dimethyl-1-adamantanamine hydrochloride and 5-methyl-1-adamantanamine 3-carboxylic acid.

27. A method for making an aqueous gel comprising:

placing a dipeptide of claim 1 in water under conditions to form a gel and allowing the gel to form.

28. A method for making an aqueous gel comprising:

placing a dipeptide of claim 13 in water under conditions to form a gel and allowing the gel to form.

* * * * *